United States Patent
Voisard et al.

(10) Patent No.: US 10,111,696 B2
(45) Date of Patent: Oct. 30, 2018

(54) IMPLANT

(75) Inventors: Cyril Voisard, Oberdorf (CH); Christian Brunner, Bern (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 13/593,966

(22) Filed: Aug. 24, 2012

(65) Prior Publication Data

US 2013/0053898 A1  Feb. 28, 2013

Related U.S. Application Data

(60) Provisional application No. 61/609,913, filed on Mar. 12, 2012, provisional application No. 61/527,609, filed on Aug. 25, 2011.

(51) Int. Cl.
*A61B 17/86* (2006.01)
*A61B 17/84* (2006.01)
(Continued)

(52) U.S. Cl.
CPC ............ *A61B 17/866* (2013.01); *A61B 17/84* (2013.01); *A61B 17/846* (2013.01); *A61B 17/86* (2013.01);
(Continued)

(58) Field of Classification Search
CPC . A61B 17/8061; A61B 17/8057; A61B 17/80; A61B 17/8085; A61B 17/846;
(Continued)

(56) References Cited

U.S. PATENT DOCUMENTS 4,737,143 A * 4/1988 Russell ................. A61M 25/02 128/DIG. 26
4,936,856 A * 6/1990 Keller ................. A61F 2/30721 623/22.36

(Continued)

FOREIGN PATENT DOCUMENTS

EP  0698382 A2  2/1996
EP  1454602 A1  9/2004
(Continued)

OTHER PUBLICATIONS

International Search Report and Written Opinion for International Application No. PCT/US2012/052213, dated Oct. 31, 2012.
(Continued)

*Primary Examiner* — Matthew Lawson
*Assistant Examiner* — Amy Sipp
(74) *Attorney, Agent, or Firm* — Morgan, Lewis & Bockius LLP

(57) ABSTRACT

An implant includes a section made of polymer, wherein at least a portion of the section has a layer of a polymerizable and/or cross-linkable material. A method for fixation of a bone plate having several plate holes using the implant includes removing a cover sheet protecting the layer of polymerizable and/or cross-linkable material, activating the layer of polymerizable and/or cross-linkable material with electromagnetic energy or with moisture, introducing the implant into one of the plate holes of the bone plate when the bone plate is positioned on a bone, pressing on an end of the implant in order to contact the activated layer of polymerizable and/or cross-linkable material with the bone underneath the bone plate, and allowing the activated and pressurized layer of polymerizable and/or cross-linkable material to polymerize and/or cross-link and to adhere to the bone.

25 Claims, 4 Drawing Sheets

(51) Int. Cl.
  *A61L 27/34* (2006.01)
  *A61L 24/04* (2006.01)
  *A61L 24/06* (2006.01)
  *A61B 17/80* (2006.01)
  *A61B 17/66* (2006.01)

(52) U.S. Cl.
  CPC ............ *A61L 24/046* (2013.01); *A61L 24/06* (2013.01); *A61L 27/34* (2013.01); *A61B 17/66* (2013.01); *A61B 17/80* (2013.01); *A61B 17/8042* (2013.01); *A61B 17/8052* (2013.01)

(58) Field of Classification Search
  CPC ..... A61B 17/68; A61B 17/84; A61B 17/7059; A61B 17/866; A61B 2017/8655; A61F 2/28; A61F 2002/3401; A61F 2002/348; A61L 27/34; A61L 27/28; A61L 27/306; F16B 11/006; F16B 13/141; F16B 13/142; F16B 39/225; F16B 37/048; Y10T 403/47; Y10T 403/471; Y10T 403/472; C08G 18/10; C08F 265/02; C08F 222/1006; C09D 151/00
  USPC ..... 606/70, 71, 76, 280, 286, 291, 298, 300, 606/302, 319, 322, 325, 329, 331, 907, 606/910; 623/16.11, 22.32, 22.39, 23.36, 623/23.37, 23.57, 23.59, 23.6; 411/82; 403/265–267
  See application file for complete search history.

(56) References Cited

U.S. PATENT DOCUMENTS

| | | | |
|---|---|---|---|
| 5,163,960 A | 11/1992 | Bonutti | |
| 5,520,690 A * | 5/1996 | Errico | A61B 17/7037 606/287 |
| 5,609,648 A * | 3/1997 | Oehy | A61F 2/30744 623/22.19 |
| 5,925,077 A * | 7/1999 | Williamson | A61B 17/1666 623/22.34 |
| 6,428,542 B1 | 8/2002 | Michelson | |
| 6,692,498 B1 * | 2/2004 | Niiranen et al. | 606/70 |
| 6,875,427 B1 | 4/2005 | DeVore et al. | |
| 7,097,645 B2 * | 8/2006 | Michelson | 606/71 |
| 7,842,037 B2 * | 11/2010 | Schulze | 606/71 |
| 7,938,831 B2 * | 5/2011 | Leroux et al. | 606/86 R |
| 8,080,043 B2 * | 12/2011 | Tormala et al. | 606/286 |
| 8,298,292 B2 * | 10/2012 | Swords et al. | 623/23.72 |
| 8,529,934 B2 * | 9/2013 | Desai et al. | 424/423 |
| 8,672,596 B2 * | 3/2014 | Condliff et al. | 411/82 |
| 8,728,082 B2 * | 5/2014 | Fritzinger | A61B 17/80 606/286 |
| 8,808,335 B2 * | 8/2014 | Biedermann | 606/291 |
| 8,840,613 B2 * | 9/2014 | Roller et al. | 606/77 |
| 8,882,506 B2 * | 11/2014 | Drapeau et al. | 433/172 |
| 8,894,695 B2 * | 11/2014 | Moore et al. | 606/286 |
| 8,900,620 B2 * | 12/2014 | Fulmer et al. | 424/426 |
| 8,906,091 B2 * | 12/2014 | Duda et al. | 623/16.11 |
| 2002/0095158 A1 | 7/2002 | Dixon et al. | |
| 2002/0128670 A1 * | 9/2002 | Ulmsten et al. | 606/151 |
| 2003/0181979 A1 * | 9/2003 | Ferree | 623/17.11 |
| 2004/0133205 A1 | 7/2004 | Thramann et al. | |
| 2005/0033430 A1 * | 2/2005 | Powers | A61B 17/7059 623/17.11 |
| 2005/0085817 A1 * | 4/2005 | Ringeisen | 606/69 |
| 2005/0107870 A1 * | 5/2005 | Wang | A61L 31/10 623/1.44 |
| 2005/0177162 A1 * | 8/2005 | McLeod | A61B 17/8028 606/70 |
| 2006/0095138 A1 | 5/2006 | Truckai et al. | |
| 2006/0155282 A1 * | 7/2006 | Vese | 606/69 |
| 2006/0224242 A1 * | 10/2006 | Swords | A61B 17/8085 623/17.19 |
| 2007/0190229 A1 * | 8/2007 | Beckman et al. | 427/2.1 |
| 2007/0233120 A1 * | 10/2007 | Thramann | A61B 17/7059 606/294 |
| 2008/0109081 A1 * | 5/2008 | Bao | A61F 2/32 623/17.15 |
| 2008/0154266 A1 * | 6/2008 | Protopsaltis | A61B 17/7013 606/76 |
| 2008/0234754 A1 * | 9/2008 | McCarthy | A61B 17/00491 606/298 |
| 2008/0262613 A1 | 10/2008 | Gogolewski | |
| 2009/0024161 A1 | 1/2009 | Bonutti et al. | |
| 2009/0240337 A1 * | 9/2009 | Myung | A61L 27/34 623/18.11 |
| 2011/0045030 A1 * | 2/2011 | Desai et al. | 424/400 |
| 2011/0098760 A1 * | 4/2011 | Griffiths et al. | 606/86 R |
| 2011/0264149 A1 * | 10/2011 | Pappalardo et al. | 606/286 |
| 2012/0059425 A1 * | 3/2012 | Biedermann | A61B 17/8042 606/291 |
| 2012/0129131 A1 | 5/2012 | Baehre et al. | |
| 2013/0116798 A1 * | 5/2013 | Farrar et al. | 623/23.62 |
| 2014/0249672 A1 * | 9/2014 | Hanssen et al. | 623/18.11 |
| 2014/0261855 A1 * | 9/2014 | Shimko et al. | 141/1 |
| 2014/0316472 A1 * | 10/2014 | Rise et al. | 606/281 |
| 2014/0316529 A1 * | 10/2014 | Rogachefsky | 623/21.14 |
| 2014/0330382 A1 * | 11/2014 | Mauldin | 623/17.11 |
| 2014/0349108 A1 * | 11/2014 | Fung et al. | 428/345 |
| 2014/0376995 A1 * | 12/2014 | Faass et al. | 403/267 |
| 2015/0033532 A1 * | 2/2015 | Van Niekerk et al. | 29/407.04 |

FOREIGN PATENT DOCUMENTS

| | | |
|---|---|---|
| EP | 2275150 A2 | 1/2011 |
| FR | 2831792 A1 | 5/2003 |

OTHER PUBLICATIONS

Communication Pursuant to Article 94(3) EPC, dated Dec. 23, 2014, for European Patent Application No. 12753652.2.

Office Action for Japanese Application No. 2014-527321, dated May 10, 2016.

* cited by examiner

IMPLANT

CROSS-REFERENCE TO RELATED APPLICATIONS

This application claims priority to U.S. Provisional Patent Application No. 61/527,609, filed Aug. 25, 2011, and claims priority to U.S. Provisional Patent Application No. 61/609,913, filed Mar. 12, 2012, each of which is incorporated herein by reference in its entirety.

FIELD OF THE INVENTION

The present invention in some embodiments generally relates to an implant for attachment to bone. More particularly, the present invention in some embodiments relates to an implant (e.g., a tack) for the fixation of a bone plate to a bone surface, the implant having one side coated with a bone adhesive or layer of a polymerizable and/or cross-linkable material that can be pressed through the opening of a plate onto the bone surface and provide a reliable adhesion strength. Some embodiments of the invention relate to an assembly comprising an implant according to the invention and a bone plate and to a method for fixation of a bone plate by means of an implant according to the invention.

BACKGROUND OF THE INVENTION

Some typical bone fixation techniques like screw insertion offer the advantage of reliability and speed but have drawbacks, among them are the damages caused to bone by drilling and tapping and the possibility of bone splitting following the screw insertion. In case of revision, the insertion of a rescue screw may be difficult or impossible. Moreover, for small, thin, bony structures, as can be found for example in the midfacial area, screw insertion is often difficult because of the limited available screw purchase.

Thus, there remains a need for an improved adhesive fixation technique avoiding the need for invasive insertion of a screw.

BRIEF SUMMARY OF THE INVENTION

The present invention in some embodiments relates to an implant for implantation in a patient comprising a rear end for manipulating the implant and a front end for contacting a bone surface, wherein the front end comprises an uncured layer of a polymerizable and/or cross-linkable material.

Said polymerizable and/or cross-linkable material, in some embodiments, may include a thermoplast, thermoset, elastomer, duromer or a resorbable polymer. In some embodiments, the polymerizable or cross-linkable material is nonresorbable. The layer of polymerizable or cross-linkable material can be applied to the implant, which may in a form of a rigid tack. In one such embodiment, the tack can include or be made of a biocompatible and biostable polymer, for example, polyether ether ketone (PEEK) or, in other embodiments, can be made of fully reacted poly (methyl methacrylate) (PMMA). In some embodiments, the tack is made at least partially or entirely from a nonresorbable material. In other embodiments, the tack is made from a resorbable material. In some embodiments, both the tack and the layer of polymerizable and/or cross-linkable material are resorbable.

In some embodiments, the lower side of the tack can be coated with a thin, well-controlled layer of the polymerizable and/or cross-linkable material, which can be activated with UV light or alternatively with moisture. For example, in some embodiments, a well-controlled layer of polymerizable and/or cross-linkable material may have characteristics such as a defined thickness, defined chemistry, and homogeneity. In some embodiments, the layer of a polymerizable and/or cross-linkable material can be activated just before insertion by irradiation with visible or UV light and then the tack can be pressed onto a surface, e.g., a bone surface. In some embodiments, the tack can be inserted into an opening of a bone plate to secure the bone plate onto a bone surface. The combined effect of pressure with light will ensure a good activation of the layer of a polymerizable and/or cross-linkable material and a good adhesion of the tack to the surface.

In some embodiments the implant comprises a section made of a transparent polymer adjacent to the front end. In some embodiments, the transparent polymer section extends from the front end to the rear end of the implant. This configuration, in some embodiments, permits the advantage that electromagnetic energy, e.g., visible or UV light can be transmitted from the rear end of the implant through the transparent section to the layer of polymerizable and/or cross-linkable material to activate said layer.

In a further embodiment of the implant said layer of polymerizable and/or cross-linkable material comprises a polymerizable amphiphilic monomer. The surface characteristics of cortical bone and metallic implants are dissimilar; therefore in some embodiments the chemistry of the adhesive layer should be compatible with two antagonist medias. The use of an amphiphilic layer of a polymerizable and/or cross-linkable material that is hydrophilic and hydrophobic simultaneously solves this problem according to some embodiments.

In some embodiments of the implant, said amphiphilic monomer comprises a component selected from the group of branched or linear, substituted or unsubstituted, saturated or partially unsaturated $C_{10}$-$C_{30}$ alkyl-, alkenyl-, alkylaryl-, aryl-, cycloalkyl-, alkylcycloalkyl-, alkylcykloaryl-carboxylates, -phosphates, or -sulfates or mixtures thereof.

In yet another embodiment of the implant said amphiphilic monomer is at least one component selected from the group of the linear unsubstituted $C_{10}$-$C_{20}$ alkyl-carboxylates or alkyl-sulfates, or their alkali- or earth alkali-salts, respectively, preferably laurate, stearate, palmitate, myristate, oleate, behanate, dodecylsulfate, preferably as alkali- or earth alkali-salts or mixtures thereof.

In another embodiment said implant is enclosed in a sterile pack. In some embodiments, the sterile pack is configured to block exposure of the implant to radiation. In some embodiments, the sterile pack is made from a material opaque to visible and/or UV-light.

In a further embodiment of the implant, said polymerizable and/or cross-linkable material is a moisture-activated isocyanate leading to a polyurethane. Therewith an advantage can be achieved, according to some embodiments, in that the layer of a polymerizable and/or cross-linkable material can be activated with moisture.

In some embodiments of the implant, said implant is configured as a tack, pin, screw or bolt with a front end and a rear end and wherein said layer of a polymerizable or cross-linkable material is attached to said front end.

In some embodiments where said implant is configured as a pin, the pin can be attached to and used for repositioning of a bone fragment. In some embodiments, this configuration permits that a reposition instrument or an internal or external fixator can be attached to the pins. In some embodiments of the implant, said pin has a length L of minimum about 45 mm, preferably minimum about 50 mm. In still another embodiment of the implant said pin has a length L of maximum about 110 mm, preferably maximum about 100 mm.

In a further embodiment of the implant said layer is protected by a removable cover sheet, preferably a multi-layer cover sheet. The multi-layer cover sheet may comprise e.g., a thicker paper layer and a thinner anti-adhesion layer destined for direct contact with said layer of polymerizable and/or cross-linkable material.

In some embodiments of the implant, the implant includes a polymer section. In some embodiments, the polymer section extends from the rear end to the front end of the implant. In some embodiments of the implant, said polymer section is rigid. In some embodiments, said polymer section is transparent to visible light and/or UV irradiation. This configuration according to some embodiments permits an advantage that the implant, e.g., in the form of a tack for fixation of a bone plate, can be pressed through the bone plate opening as far as the lower side of the tack comprising the layer of polymerizable and/or cross-linkable material contacts the bone surface and then the layer of a polymerizable and/or cross-linkable material can be activated with visible or UV light transmitted through the rigid tack that is transparent to visible or UV light. In some embodiments of the implant, said polymer section is made of a biocompatible and biostable polymer, preferably PEEK or PMMA.

In a further embodiment of the implant said layer of a polymerizable and/or cross-linkable material comprises a material chosen from the following group: epoxy resins, fibrin adhesive, polyurethane. In a further embodiment of the implant said polymerizable or cross-linkable material is a cyanoacrylate.

In another embodiment of the implant said layer of a polymerizable and/or cross-linkable material has a thickness of about 100 nm to about 1000 µm, preferably of about 100 µm to about 500 µm.

In another embodiment said implant is a bone plate comprising said layer of a polymerizable or cross-linkable material at its lower side destined to be contacted with bone.

In another embodiment said implant, preferably at its polymer section comprises a suture.

In accordance with another aspect, an assembly is provided which comprises an implant according to the invention and a bone plate with several plate holes wherein said implant is a fixation element with a rear side, one or more lateral sides and a front side for insertion into said plate holes. Further, said front side is provided with said layer of a polymerizable or cross-linkable material.

In one embodiment of the assembly, said lateral sides of said implant are provided at least partially with said layer of a polymerizable or cross-linkable material.

In a further embodiment of the assembly at least part of the surfaces of said fixation element and of said plate holes comprise interlocking means, preferably in the form of hooks and eyelets. An advantage of this configuration according to some embodiments is a better interlocking and fixation of the fixation elements in the plate holes.

According to a further aspect of the invention, there is provided a method for fixation of a bone plate having several plate holes by means of a longitudinal fixation implant with a front and rear end, comprising a polymer section at its front end with a layer of a polymerizable or cross-linkable material protected by a removable cover sheet. The method comprising the following steps: a) removing said cover sheet; b) activating said polymerizable or cross-linkable material with electromagnetic energy or with moisture; c) introducing said longitudinal fixation implant into one of said plate holes of said plate positioned on a bone; d) pressing on said rear end in order to contact said activated layer of said front end with the bone underneath said bone plate: and e) allowing said activated and pressurized layer to polymerize or cross-link and to adhere to the bone.

In another embodiment of the method, said implant comprises a section made of a transparent polymer adjacent to the front end of the implant; and wherein step c) is performed before step b) which particularly comprises activating said polymerizable or cross-linkable material with electromagnetic energy through said section made of a transparent polymer.

In a further embodiment the method comprises the further step of removing the periosteum of said bone where said front end of said longitudinal fixation implant is to be pressed against said bone.

In accordance with another embodiment, there is a method for repositioning bone fragments by means of one or more pins with a front end, a rear end and an uncured layer of a polymerizable or cross-linkable material at said front end. The method includes the steps of a) performing an incision each in the region of each bone fragment to be reduced; b) removing said cover sheet from said pin; c) activating said polymerizable or cross-linkable material with electromagnetic energy or with moisture; d) introducing said pin in the soft tissue; e) pressing on said rear end in order to contact said activated layer of said front end with the respective bone fragment; f) allowing said activated and pressurized layer to polymerize or cross-link and to adhere to the bone; repeating steps b) to f) for each bone fragment to be repositioned; and reducing the bone fracture by using said one or more pins as a reduction aid.

BRIEF DESCRIPTION OF THE DRAWINGS

Several embodiments of the invention will be described in the following by way of example and with reference to the accompanying drawings in which.

DETAILED DESCRIPTION OF THE INVENTION

Figure 1:
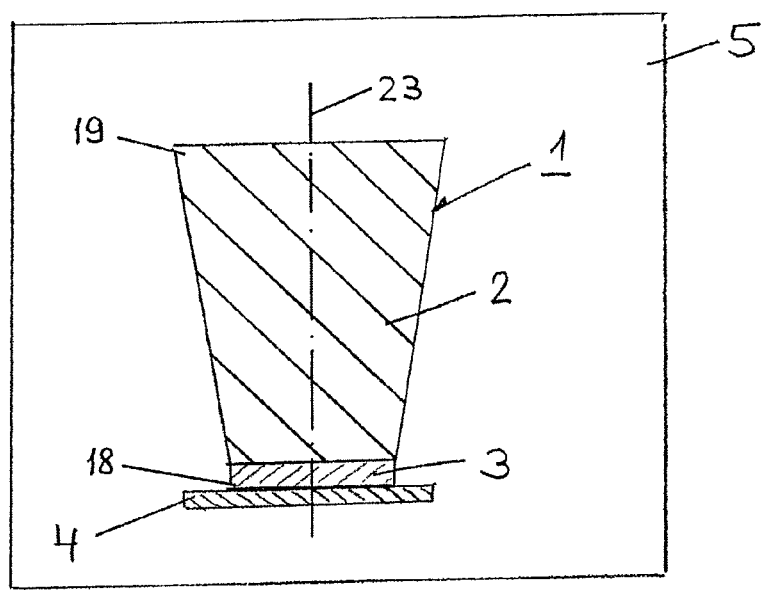
FIG. 1 illustrates a section through an implant according to one embodiment of the invention in the form of a fixation element for a bone plate.

FIG. 1 illustrates an embodiment of the implant 1 in the form of a fixation element for a bone plate that is positioned over bone. In some embodiments, implant 1 may be configured as a tack, screw, bolt, or the like. In some embodiments, implant 1 is substantially cylindrical in shape. In some embodiments, implant 1 (e.g., in the form of a tack) includes a cylindrical core having substantially constant cross-sectional dimension (e.g., diameter) along its length which may be threaded or unthreaded. In other embodiments, as shown in FIG. 1, the tack may have a tapered or varying cross-sectional dimension (e.g., diameter) along its length. In some embodiments, for example, implant 1 may be in the form of a conical tack.

Implant 1, in some embodiments, has a longitudinal shape with a longitudinal axis 23, a rear end 19 and a front end 18. In some embodiments, implant 1, or at least a portion thereof (e.g., rear end 19), is made from a substantially rigid material. According to one embodiment, implant 1 is unthreaded. In some embodiments, implant 1 is tapered from rear end 19 to front end 18 such that a cross-sectional dimension (e.g., a diameter) of implant 1 at front end 18 is less than the cross-sectional dimension at rear end 19. In some embodiments front end 18 is substantially flat. In other embodiments, front end 18 defines a concave surface. In some embodiments, front end 18 is contoured to substantially match the curvature of the bone surface to be contacted. In some embodiments, front end 18 is made from a compliant material that can bend to match the contour of the bone surface when pressed against the bone surface. In some embodiments, front end 18 is not configured to penetrate through the surface of a bone. In some embodiments, front end 18 is not configured to penetrate further than the cortical layer of a bone. In some embodiments, front end 18 is provided with an uncured layer 3 of a polymerizable and/or cross-linkable material which is configured to adhere or attach implant 1 to bone, as will be described further herein. In some embodiments, layer 3 may be protected with a removable coversheet 4 prior to implantation.

Figure 2:
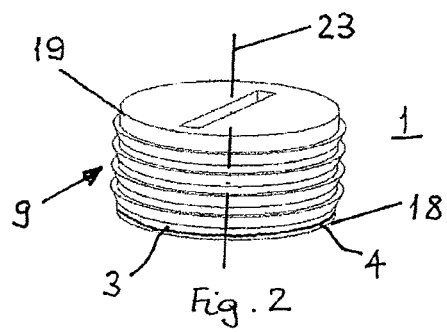
FIG. 2 illustrates a perspective view of another embodiment of the implant according to one embodiment of the invention in the form of a threaded tack for a bone plate.
Figure 3:
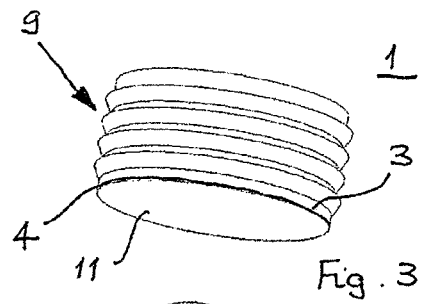
FIG. 3 illustrates another perspective view of the embodiment of the implant according to FIG. 2.

FIGS. 2 and 3 illustrate another embodiment of the implant 1. The implant 1 according to this embodiment is configured as a fixation element 9 in the form of a threaded tack with a layer 3 of a polymerizable and/or cross-linkable material. The layer 3 is arranged at the front side 11 of front end 18 of the fixation element 9 for contact with the surface of a bone. In some embodiments, fixation element 9 includes one or more lateral sides which may be provided at least partially with the layer 3 of a polymerizable and/or cross-linkable material. In some embodiments, layer 3 can be configured as described with regards to FIG. 1. Before the fixation element 9 is used the layer 3 can be protected with a removable cover sheet as described with regards to FIG. 1. In some embodiments, rear end 19 of the threaded tack is configured to receive a tool for screwing or driving the threaded tack into a bone plate. In some embodiments, rear end 19 further defines a cavity for receiving the tool.

In some embodiments, implant 1 or at least a portion thereof is made of a material transparent to visible and UV radiation and includes, at its front end 18, a layer 3 of a polymerizable and/or cross-linkable material. In some embodiments, implant 1 comprises at least a section made of a transparent and preferably rigid material adjacent to front end 18. This configuration permits the advantage that electromagnetic energy, e.g., visible or UV light can be transmitted from the through the transparent section to layer 3 of polymerizable and/or cross-linkable material to activate said material of layer 3 according to some embodiments. In some embodiments, the transparent section is made from a transparent polymer. In some embodiments, the transparent section is made from a transparent thermoplastic polymer. In some embodiments, the transparent section is made from polyether ether ketone (PEEK) or poly(methyl methacrylate) (PMMA). In some embodiments, the transparent section is made from a glass. In some embodiments, the transparent section further includes a suture.

In some embodiments, layer 3 has a thickness of about 100 nm to about 1000 µm, preferably of about 100 µm to about 500 µm. In some embodiments, layer 3 includes a polymerizable and/or cross-linkable material that forms a nonresorbable material when polymerized and/or cross-linked. In some embodiments, layer 3 includes a catalyst responsive to UV light and configured to cause polymerization and/or cross-linking of the polymerizable and/or cross-linkable material of layer 3. In one embodiment, the polymerizable and/or cross-linkable material includes methyl methacrylate (MMA) with a catalyst responsive to visible or UV light.

In some embodiments, layer 3 includes a polymerizable amphiphilic monomer. In some embodiments, the amphiphilic monomer includes a component selected from the group of branched or linear, substituted or unsubstituted, saturated or partially unsaturated $C_{10}$-$C_{30}$ alkyl-, alkenyl-, alkylaryl-, aryl-, cycloalkyl-, alkylcycloalkyl-, alkylcykloaryl-carboxylates, -phosphates, or -sulfates or mixtures thereof. In other embodiments, the amphiphilic monomer is at least one component selected from the group of the linear unsubstituted $C_{10}$-$C_{20}$ alkyl-carboxylates or alkyl-sulfates, or their alkali- or earth alkali-salts, respectively, preferably laurate, stearate, palmitate, myristate, oleate, behanate, dodecylsulfate, preferably as alkali- or earth alkali-salts or mixtures thereof. In some embodiments, layer 3 includes epoxy resins, fibrin adhesive, polyurethane and combinations thereof. In some embodiments, the polymerizable and/or cross-linkable material of layer 3 is a cyanoacrylate.

In some embodiments, as illustrated in FIG. 1, the layer 3 is protected by a removable cover sheet 4 and the complete implant 1 is enclosed in a sterile pack 5 prior to implantation. In some embodiments, cover sheet 4 is preferably a multi-layer cover sheet. The multi-layer cover sheet may comprise e.g., a thicker paper layer and a thinner anti-adhesion layer configured for direct contact with said layer 3 of polymerizable and/or cross-linkable material.

In some embodiments, sterile pack 5 is made from a radiation-blocking material to prevent premature activation of the polymerizable and/or cross-linkable material. In some embodiments, sterile pack 5 is made from a material opaque to visible and/or UV-light. In some embodiments, sterile pack 5 is configured to isolate implant 1 from moisture.

In use, according to certain embodiments of the invention, implant 1 is removed from sterile pack 5 and cover sheet 4 is removed to expose layer 3. Implant 1 (e.g., in the form of a tack or other fixation element) is pushed through a plate hole of a bone plate positioned on a bone until front end 18 of implant 1 with the layer 3 of a polymerizable and/or cross-linkable material contacts the bone beneath the bone plate. In some embodiments, a pressure is applied to implant 1 (e.g., on rear end 19) to maintain contact between the bone and layer 3. In some embodiments, implant 1 makes contact with but does not penetrate through the surface of the bone. In some embodiments, implant 1 does not penetrate into the cortical layer of the bone. In some embodiments, implant 1 penetrates into the bone no further than the cortical layer of the bone.

As described herein, implant 1 or a section thereof adjacent to front end 18 in some embodiments is made from a transparent material. In some embodiments, by directing visible or UV light from a light source (e.g., UV lamp or a dental curing lamp) through the transparent material of implant 1, layer 3 is activated and polymerizes and/or cross-links to adhere to the bone portion against which it has been pushed under pressure. In some embodiments, pressure may be applied to the implant 1 by hand. In other embodiments, pressure may be applied by a lightguide of the lightsource (e.g., UV lamp). The combined effect of pressure with light will ensure a good activation of the polymerizable and/or cross-linkable material of layer 3 and a good adhesion of implant 1 to the bone. In some embodiments, pressure is maintained on implant 1 for sufficient time for substantially the entire layer 3 to polymerize and/or cross-link. In some embodiments, layer 3 is configured to polymerize and/or cross-link in less than 5 minutes from activation. In some embodiments, layer 3 is configured to polymerize and/or cross-link in less than 1 minute from activation. In some embodiments, layer 3 is configured to polymerize and/or cross-link in about 30 seconds to about 2 minutes after pressing implant 1 against the bone portion, preferably in less than 1 minute. In some embodiments, layer 3 is configured to polymerize and/or cross-link in 30 seconds or less after pressing the tack against the bone portion. In some embodiments, layer 3 is configured to form chemical bonds the bone during polymerization and/or cross-linking, thereby adhering implant 1 to the bone. Adherence to the bone can be enhanced, according to some embodiments, by removing the periost from the bone surface at the location where the tack is to be positioned. In some embodiments, implant 1 is configured to adhere directly to the bone surface. In some embodiments, the adhesion strength of implant 1 to the bone is at least 10 MPa.

In some embodiments, a layer of primer material is first applied to the bone surface on which layer 3 is positioned. In some embodiments, the primer material is selected to react with and bind to the bone surface and layer 3 during polymerization and/or cross-linking. In some embodiments, the primer material is configured to etch the mineralized portion of the bone and penetrate into the bone surface. In some embodiments, the primer material is configured to chemically cross-link with amino acids and be capable of forming chemical bonds with organic parts (e.g., proteins) of the bone. In some embodiments, the primer material includes chemical groups (e.g., methacrylates) that are cross-linkable with the material of layer 3. Example primer materials that may be used in certain embodiments include acidic methacrylate or dimethacrylate monomers and 4-methacryloyloxyethyl trimellitate anhydride (4-META).

In a further embodiment, layer 3 of the polymerizable and/or cross-linkable material of the light activation type can be activated just before insertion of implant 1 into the plate hole of the bone plate by irradiating the polymerizable and/or cross-linkable material of layer 3 with visible or UV light. In some embodiments, the light to activate the polymerizable and/or cross-linkable material is supplied by a UV lamp, a dental curing lamp, or other light source known in the art. The tack with the activated layer 3 can be then pressed through the plate opening and onto the surface of a bone.

The amount of light and duration of exposure used to activate layer 3 to initiate polymerization and/or cross-linking, in some embodiments, can be adjusted based on the amount of and type of monomer contained in layer 3. In some embodiments, the activation time before insertion of the tack is less than 30 seconds, preferably about 5 seconds. In some embodiments, activation of the polymerizable and/or cross-linkable material can be achieved by exposure to light for about 5 seconds to about 1 minute, preferably less than 1 minute. In some embodiments, activation of the polymerizable and/or cross-linkable material can be achieved by exposure to light for about 5 seconds to about 30 seconds. In some embodiments, exposure to light should not exceed 1 minute. In some embodiments, activation of the polymerizable and/or cross-linkable material can be achieved by exposure to light for about 5 minutes. In other embodiments, activation of the polymerizable and/or cross-linkable material can be achieved by exposure to light for less than 5 minutes. In some embodiments, the light intensity to activate the polymerizable and/or cross-linkable material is on the order of 1000 mW/cm$^2$.

In some embodiments, layer 3 includes a moisture-activated polymerizable and/or cross-linkable material. According to these embodiments, layer 3 can be activated by exposing layer 3 to moisture prior to contacting the bone surface. In some embodiments, moisture-activated polymerizable and/or cross-linkable material is a moisture-activated isocyanate that polymerizes into a polyurethane.

In some embodiments front end 18 is substantially flat. In other embodiments, front end 18 defines a concave surface. In some embodiments, front end 18 is contoured to substantially match the curvature of the bone surface to be contacted. In some embodiments, front end 18 is made from a compliant material that can mold to the contour of the bone surface when pressed against the bone surface. In some embodiments, the compliant material can include a softened base material, silicone, or flexible biocompatible polymer material.

Figure 4:
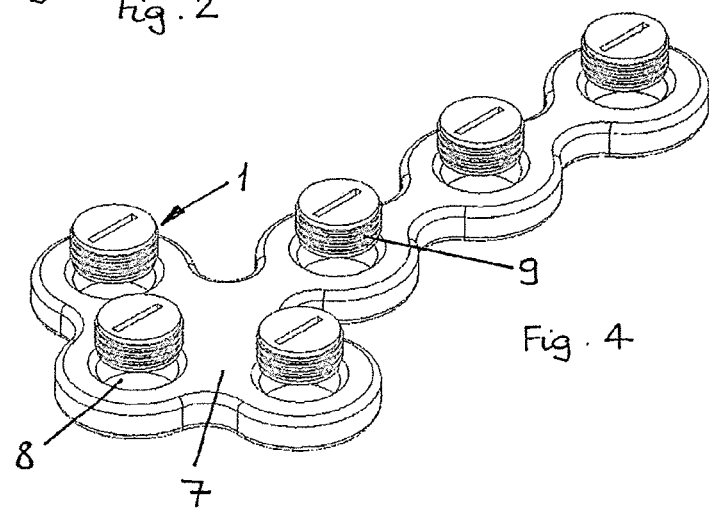
FIG. 4 illustrates a perspective view of an embodiment of an assembly according to one embodiment of the invention.

FIGS. 4 to 7 illustrate the use of an exemplary embodiment of the assembly including a plurality of fixation elements 9 according to FIGS. 2 and 3 in combination with a bone plate 7 for the treatment of a base proximal phalanx fracture. The bone plate 7 has several plate holes 8 with an internal thread into which a fixation element 9 each can be inserted as illustrated in FIG. 4.

Figure 7:
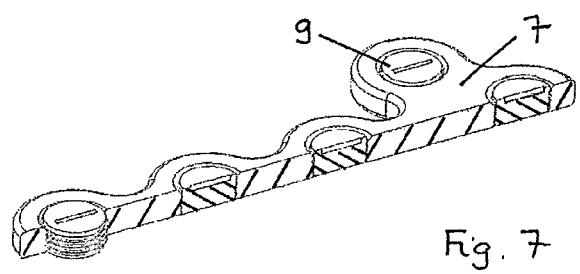
FIG. 7 illustrates a sectional view of the embodiment of the assembly according to the embodiment of FIG. 4 used for fixation of a base proximal phalanx fracture.

Commonly, hand fractures are treated with bone plates 7 either straight or T-shaped as illustrated in FIG. 4 that are fixed on the phalanx or metacarpal with bone screws, providing a good stability. According embodiments of the present invention, bone plate 7 can be attached to the bone with fixation elements 9, e.g., the tacks according to FIGS. 2 and 3. In some embodiments, fixation elements 9 are made of PMMA and have their front side 11 coated with a layer 3 of a polymerizable and/or cross-linkable material. After removal of the periosteum and activation of the layer 3 as described herein, fixation element 9 is screwed into a plate hole 8 and forwarded as far as the front side 11 of the fixation element 9 abuts on the bone surface. In some embodiments, at least part of the surfaces fixation element 9 and said plate hole 8 include interlocking means, for example, in the form of hooks and eyelets. In some embodiments, fixation elements 9 are sized and dimensioned such that the rear ends 19 of each fixation element is substantially flush with a top surface of bone plate 7 when fully screwed into plate holes 8 as shown in FIG. 7. In some embodiments, fixation element 9 makes contact with but does not penetrate through the surface of the bone. In some embodiments, fixation element 9 does not penetrate into the cortical layer of the bone. In some embodiments, fixation element 9 penetrates into the bone no further than the cortical layer of the bone.

Figure 5:
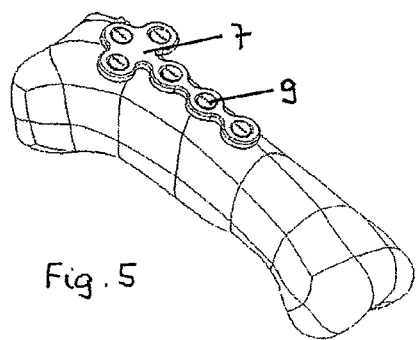
FIG. 5 illustrates a perspective view from distal of the embodiment of the assembly according to the embodiment of FIG. 4 used for fixation of a base proximal phalanx fracture.
Figure 6:
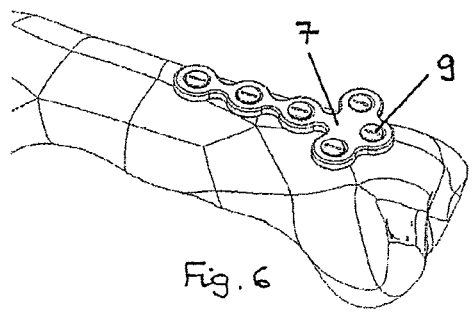
FIG. 6 illustrates a perspective view from proximal of the embodiment of the assembly according to the embodiment of FIG. 4 used for fixation of a base proximal phalanx fracture.

FIGS. 5 and 6 illustrate the bone plate 7 fixed to the proximal phalanx by means of the fixation elements 9 which are adhered on the surface of the proximal phalanx.

Figure 8:
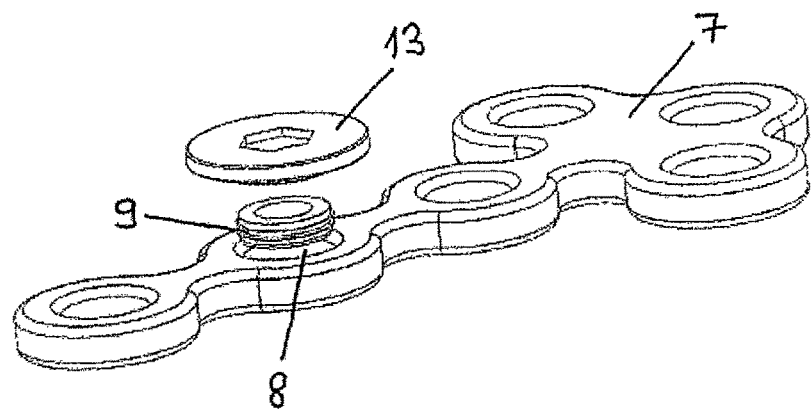
FIG. 8 illustrates a perspective view of another embodiment of the assembly according to one embodiment of the invention.

FIG. 8 illustrates another embodiment of the assembly wherein each fixation element 9 is locked in the plate hole 8 by means of a cap 13. In some embodiments, cap 13 is configured to at least partially cover the top of fixation element 9. In some embodiments, cap 13 is configured to screw into the plate hole 8 on top of the fixation element 9. In some embodiments, cap 13 is configured to prevent exit of fixation element 9 from hole 8. In some embodiments, cap 13 is configured to prevent soft tissue ingrowth into hole 8. In some embodiments, cap 13 is configured to receive a tool for screwing or driving cap 13 into bone plate 7. In some embodiments, a surface of cap 13 defines a cavity for receiving the tool.

Figure 9:
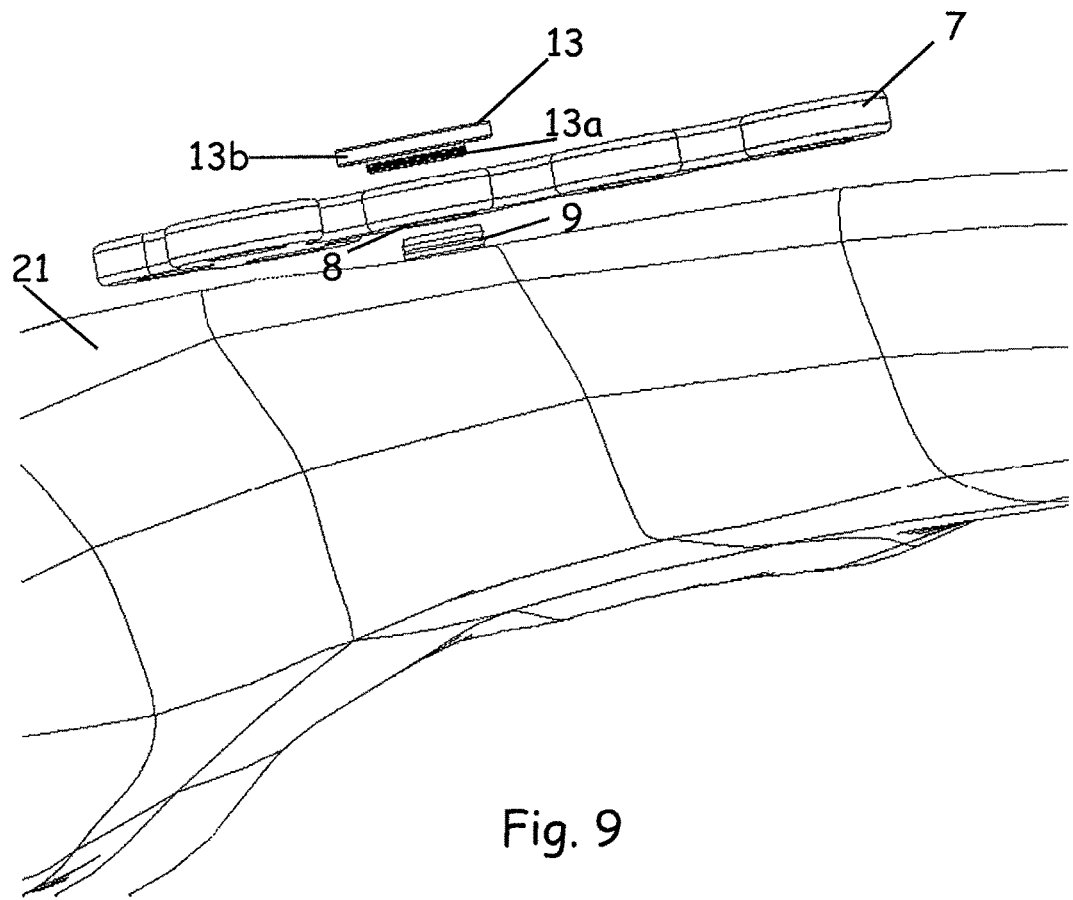
FIG. 9 illustrates an elevational view of an assembly according to one embodiment of the invention.

With reference now to FIG. 9, in some embodiments a method of the present invention includes first securing fixation element 9 to a surface of a bone 21. In some embodiments, fixation element 9 includes a front end coated with a layer of a polymerizable and/or cross-linkable material which is activated as described herein and contacted to the surface of bone 21 to secure fixation element 9 to bone 21. For example, in some embodiments, the layer of polymerizable and/or cross-linkable material is activated by exposure to electromagnetic energy, light, or moisture and then pressed against the surface of bone 21. Similar to the embodiments of FIGS. 1 to 3, the layer of polymerizable and/or cross-linkable material can be protected by a removable cover sheet which is removed prior to activation.

After securing fixation element 9 to the surface of bone 21, bone plate 7 may then be coupled with fixation element 9. In some embodiments, bone plate 7 is coupled with fixation element 9 by positioning bone plate 7 to receive fixation element 9 in hole 8 of bone plate 7 while fixation element 9 is secured to bone 21. In some embodiments, fixation element 9 is coupled with and secured to bone plate 7 (e.g., within hole 8) by an interference, friction, or snap fit. In other embodiments, hole 8 is provided with internal threads and fixation element 9 is configured to thread into hole 8 of bone plate 7.

In further embodiments, a cap 13 as described herein may be provided over hole 8 to cover an exposed end (e.g., rear end) of fixation element 9. Cap 13 according to some embodiments may be configured to prevent soft tissue ingrowth into hole 8. In some embodiments, cap 13 is secured to bone plate 7 after bone plate 7 is coupled with fixation element 9. In some embodiments, cap 13 includes a threaded portion 13a configured to thread into hole 8 of bone plate 7 and a top portion 13b having a diameter larger than the diameter of hole 8. In other embodiments, cap 13 may be secured into hole 8 of bone plate 7 by an interference, friction, or snap fit.

Figure 10:
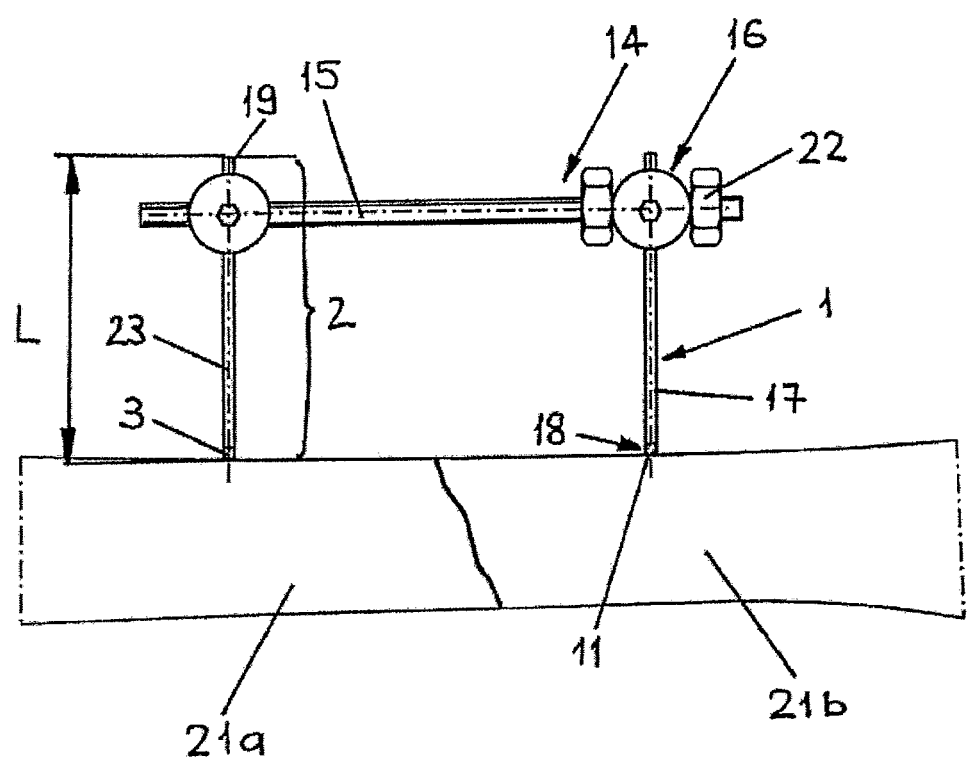
FIG. 10 illustrates a further use of the implant according to an embodiment of the invention for repositioning bone fragments.

FIG. 10 illustrates a further example of the use of the implant 1 in the case of repositioning bone fragments 21a; 21b. The implant 1 according to this example is configured as a pin 17. Each pin 17 is affixed to a bone fragment 21a; 21b. The pin 17 has a length L that is dimensioned so that, e.g., a reposition forceps can be positioned at the rear portion of one or each of the two pins 17. In some embodiments, pin 17 has a length L of at least 40 mm. In some embodiments, pin 17 has minimum length of about 45 mm to about 50 mm. In some embodiments, pin 17 has a maximum length of about 100 mm to about 110 mm.

The pin 17 comprises a longitudinal axis 23, a front end 18 with a front side 11, a rear end 19 and a section 2 which, in some embodiments, is made of a rigid material and which includes a layer 3 of a polymerizable and/or cross-linkable material as described herein. The section 2 can extend from the rear end 19 to the front end 18 of said pin 17 so that said layer 3 of a polymerizable and/or cross-linkable material is located at the front side 11 of the pin 17. When said pin 17 is implanted into the human or animal body said layer 3 can contact the surface of a bone. In some embodiments, pin 17 makes contact with but does not penetrate through the surface of the bone. In some embodiments, pin 17 does not penetrate into the cortical layer of the bone. In some embodiments, pin 17 penetrates into the bone no further than the cortical layer of the bone.

In some embodiments, pin 17 can be made of a biocompatible and biostable polymer, preferably of polyether ether ketone (PEEK) or PMMA. The layer 3 can be made of a polymerizable and/or cross-linkable material, preferably MMA with a catalyst responsive to visible or UV light. Alternatively, the layer 3 of a polymerizable and/or cross-linkable material can be made of a moisture-activated isocyanate leading to a polyurethane so that the layer 3 of a polymerizable and/or cross-linkable material can be activated with moisture.

Similarly to the embodiments of FIGS. 1 to 3 the layer 3 can be protected by a removable cover sheet and the complete implant 1 can be enclosed in a sterile pack. In use, pin 17 is removed from the sterile pack and the cover sheet, when present, is removed. Pin 17 is subsequently pushed through the soft tissue until the front side 11 of the pin 17 with the layer 3 of a polymerizable and/or cross-linkable material attached thereto contacts the bone.

In some embodiments, layer 3 of a polymerizable and/or cross-linkable material can be activated just before insertion into the soft tissue, and the pin 17 with activated layer 3 can be pushed through the soft tissue until the front side 11 of the pin 17 with the layer 3 of a polymerizable and/or cross-linkable material attached thereto contacts the bone. In some embodiments, layer 3 includes a light-activated polymerizable and/or cross-linkable material and can be activated by exposure to light just before insertion into the soft tissue. In alternative embodiments, layer 3 includes a moisture-activated polymerizable and/or cross-linkable material (e.g., a moisture-activated isocyanate leading to a polyurethane) and can be activated with moisture just before insertion into the soft tissue.

Furthermore as shown in FIG. 10, according to some embodiments, a reposition instrument 14 in the form of a distractor or traction instrument or an external fixator can be attached to the two pins 17. In some embodiments, the reposition instrument 14 can include a threaded connector rod 15 and a clamping device 16 each for coupling the reposition instrument 14 to the pins 17. A nut 22 which is laterally screwed onto the threaded connector rod 15 is configured to push the two bone fragments 21a; 21b towards each other. A second nut is screwed onto the threaded connector rod 15 between the two pins 17 so that the two bone fragments 21a; 21b can be distracted when required. Alternatively, in other embodiments, a universal chuck with a T-handle can be fixed to each pin 17 for manually reducing the bone fracture. In some embodiments, after repositioning the bone fragments 21a; 21b the reposition instrument 14 can be removed and an internal or external fixator can be affixed to the pins 17.

After the bone fracture has healed, pins 17 may be removed from the bone surface according to some embodiments through mechanical force sufficient to break the bond between layer 3 and the bone surface. In some embodiments, the bone surface where pins 17 were attached may be cleaned to remove any residual polymer material. In some embodiments, removal of pins 17 will not leave cavities in the bone because pins 17 did not penetrate into the surface of the bone.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

The invention claimed is:

1. An assembly for implantation in a patient comprising:
an implant comprising:
 a rear end for manipulating the implant;
 a front end comprising an uncured layer of a polymerizable and/or cross-linkable material, the uncured layer being configured to contact a surface of a bone and adhere the implant to the surface of the bone, wherein the front end is substantially flat and does not include an opening;
 a cylindrical core extending from the rear end of the implant to the front end of the implant;
 a section of said cylindrical core made of a rigid transparent polymer adjacent to the front end configured to transmit visible and/or UV light from the rear end of the implant to the front end of the implant; and
a bone plate comprising a plurality of plate holes, each plate hole having an internal thread,
wherein said implant is a fixation element for attaching the bone plate to the bone without the implant penetrating further than a cortical layer of the bone, the fixation element including a rear side at said rear end, one or more lateral sides, a front side at said front end for insertion into one of said plate holes, and an external thread on the cylindrical core extending from said rear side to said front side for engaging with the internal thread of said one of said plate holes, said front side being provided with said uncured layer of the polymerizable and/or cross-linkable material,
wherein the assembly is configured to be attached to the bone without the bone being penetrated further than the cortical layer of the bone.

2. The assembly according to claim 1, wherein said uncured layer comprises a polymerizable amphiphilic monomer on an outer surface of the implant.

3. The assembly according to claim 2, wherein said amphiphilic monomer comprises a component selected from the group consisting of branched or linear, substituted or unsubstituted, saturated or partially unsaturated $C_{10}$-$C_{30}$ alkyl-, alkenyl-, alkylaryl-, aryl-, cycloalkyl-, alkylcycloalkyl, alkylcykloaryl-carboxylates, -phosphates, or -sulfates, and mixtures thereof.

4. The assembly according to claim 2, wherein said amphiphilic monomer includes at least one component selected from the group consisting of the linear unsubstituted $C_{10}$-$C_{20}$ alkyl-carboxylates or alkyl-sulfates, or their alkali- or earth alkali-salts, respectively.

5. The assembly according to claim 2, wherein said amphiphilic monomer includes at least one component selected from the group consisting of laurate, stearate, palmitate, myristate, oleate, behanate, dodecylsulfate, their alkali- or earth alkali-salts, and mixtures thereof.

6. The assembly according to claim 1, wherein said polymerizable and/or cross-linkable material is a moisture-activated isocyanate capable of forming a polyurethane.

7. The assembly according to claim 1, wherein said implant is configured as a tack, pin, screw, or bolt.

8. The assembly according to claim 1, wherein said uncured layer is protected by a removable cover comprising multiple layers, the multiple layers including an anti-adhesion layer in contact with the uncured layer of the polymerizable and/or cross-linkable material.

9. The assembly according to claim 1, wherein said transparent polymer section is transparent to UV irradiation.

10. The assembly according to claim 1, wherein said uncured layer comprises a material chosen from the following group: epoxy resins, fibrin adhesives, polyurethane and combinations thereof.

11. The assembly according to claim 1, wherein said uncured layer has a thickness of 100 nm to 1000 μm.

12. The assembly according to claim 1, wherein said polymerizable and/or cross-linkable material is a cyanoacrylate.

13. The assembly according to claim 1, wherein said one or more lateral sides are provided at least partially with said layer of a polymerizable and/or cross-linkable material.

14. The assembly according to claim 1, wherein at least part of the threads of said fixation element and of said plate holes are configured to interlock.

15. The assembly according to claim 1, wherein the polymerizable and/or cross-linkable material forms a non-resorbable material when polymerized and/or cross-linked.

16. The assembly according to claim 1, wherein the implant is configured to not penetrate through the surface of the bone during implantation.

17. The assembly of claim 1, wherein the rear end and the front end of the implant have the substantially same diameter.

18. An implant for implantation in a patient comprising:
a rear end for manipulating the implant;
a front end comprising an uncured layer of a polymerizable and/or cross-linkable material, the uncured layer being configured to contact a surface of a bone and adhere the implant to the surface of the bone, wherein the front end is substantially flat and does not include an opening;
a cylindrical core extending from the rear end to the front end;
a section of said cylindrical core made of a rigid transparent polymer adjacent to the front end, wherein said rigid transparent polymer section is configured to transmit visible and/or UV light from the rear end of the implant to the front end of the implant; and
an external thread on the cylindrical core extending from the rear end to the front end, wherein the implant is provided with a removable cover comprising multiple layers adjacent to the front end, the multiple layers comprising an anti-adhesion layer in contact with the uncured layer of the polymerizable and/or cross-linkable material.

19. An assembly comprising:
    the implant according to claim 18; and
    a bone plate comprising a plurality of plate holes, each plate hole having an internal thread for engaging with the external thread of the implant, wherein said implant is a fixation element with a rear side at said rear end, one or more lateral sides, and a front side at said front end for insertion into one of said plate holes, said front side being provided with said uncured layer of the polymerizable and/or cross-linkable material,
    wherein the assembly is configured to be attached to the bone without the bone being penetrated further than a cortical layer of the bone.

20. The implant according to claim 18, wherein the implant is configured to penetrate into the surface of the bone no further than a cortical layer of the bone.

21. An assembly for attachment to a surface of a bone comprising:
    an implant having a top surface, a bottom surface opposite the top surface, and at least one hole extending through the implant from the top surface to the bottom surface, the at least one hole being externally bounded by an inner wall; and
    a fixation element comprising:
        a front end having a layer comprising polymerizable and/or cross-linkable material that is adherent to the surface of the bone when the polymerizable and/or cross-linkable material is activated, wherein the front end is substantially flat and does not include an opening;
        a rear end opposite the front end, the rear end configured to receive a tool for driving the fixation element into the at least one hole of the implant;
        a cylindrical core extending from the rear end of the implant to the front end of the implant;
        a rigid transparent section of said cylindrical core positioned between the front end and the rear end, the rigid transparent section configured to transmit visible and/or UV light to the layer of polymerizable and/or cross-linkable material; and
        a sidewall of the cylindrical core extending from the front end to the rear end, the sidewall being configured to engage the inner wall of the implant, the sidewall comprising an external thread extending from the rear end to the front end that is configured to engage with the inner wall of the implant,
    wherein the assembly is configured to be attached to the bone without the bone being penetrated further than a cortical layer of the bone.

22. The assembly of claim 21, wherein the rear end comprises a cavity for receiving the tool.

23. The assembly of claim 21, wherein the transparent section extends from the front end to the rear end.

24. The assembly of claim 21, wherein the front end further comprises a compliant material configured to bend to match a contour of the surface of the bone.

25. The assembly of claim 21, wherein the assembly is configured to be attached to the bone without the use of bone screws.

* * * * *